United States Patent [19]

Koshugi

[11] 4,356,236

[45] Oct. 26, 1982

[54] SPHERICALLY SHAPED MATERIAL COMPRISING ACYLATED PRODUCT OF DE-N-ACETYLATED CHITIN

[75] Inventor: Junichi Koshugi, Tokyo, Japan

[73] Assignee: Kureha Kagaku Kogyo Kabushiki Kaisha, Tokyo, Japan

[21] Appl. No.: 156,476

[22] Filed: Jun. 4, 1980

[30] Foreign Application Priority Data

Jun. 15, 1979 [JP] Japan .................................. 54-75401

[51] Int. Cl.³ .................... B32B 1/00; C08B 37/08
[52] U.S. Cl. ........................ 428/403; 128/DIG. 8; 252/316; 252/426; 252/448; 424/361; 427/2; 428/332; 428/402; 521/29; 536/20
[58] Field of Search ............... 252/316, 426, 448; 427/3, 2, 212; 428/332, 402, 403; 424/361; 521/29; 536/20; 128/DIG. 8

[56] References Cited

U.S. PATENT DOCUMENTS

| | | | |
|---|---|---|---|
| 2,842,049 | 7/1958 | Delangre | 536/20 X |
| 3,847,897 | 11/1974 | Dunn et al. | 536/20 |
| 3,879,376 | 4/1975 | Vanlerberghe et al. | 424/361 X |
| 3,879,377 | 4/1975 | Austin | 536/20 |
| 4,029,727 | 6/1977 | Austin et al. | 536/20 X |
| 4,111,810 | 9/1978 | Arai et al. | 210/653 |
| 4,143,201 | 3/1979 | Miyashiro et al. | 428/402 X |
| 4,255,286 | 3/1981 | Berek et al. | 428/402 X |

FOREIGN PATENT DOCUMENTS 894993 10/1953 Fed. Rep. of Germany .
48-19213 6/1973 Japan .

OTHER PUBLICATIONS

Proceedings International Conference Chitin/Chitosan, 1st 1977, Published May, 1978, G. K. Hoore et al.: "Studies on the Acetylation of Chitosan", pp. 421–429.

*Primary Examiner*—Robert A. Dawson
*Attorney, Agent, or Firm*—Wegner & Bretschneider

[57] ABSTRACT

A spherically shaped material at least the surface layer of which comprises an acylated product of de-N-acetylated chitin. The spherical material is insoluble in water, acids, alkaline solutions and organic solvents. The materials can be employed to separate materials on a column, as a base material on which enzyme is immobilized and as an adsorbent, etc.

19 Claims, 1 Drawing Figure

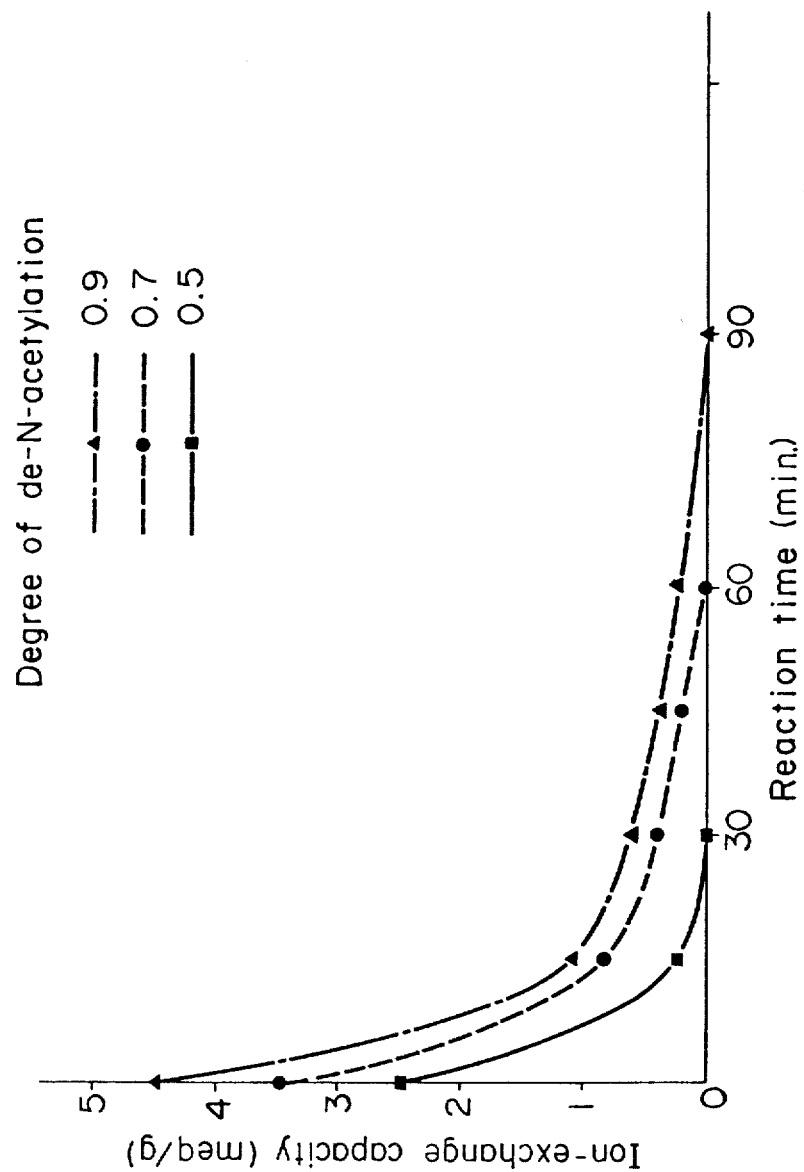

SPHERICALLY SHAPED MATERIAL COMPRISING ACYLATED PRODUCT OF DE-N-ACETYLATED CHITIN

This invention relates to a spherically shaped material comprising an acylated product of de-N-acetylated chitin. This invention also relates to a process for producing the same.

Fiberforming polysaccharides occurring in nature are divided broadly into collagen in higher animals, chitin in arthropods and lower plants and cellulose in higher plants, and the skeletons of the living things are made by the sedimentation of apatite, calcium carbonate and lignin onto the above-mentioned polysaccharide respectively. Among them, the chitin is a mucopolysaccharide of poly-N-acetyl-D-glucosamine, and its amount in nature compares favorably with the amount of cellulose in nature. However, since the chitin is a highly crystalline substance and the intermolecular bonding thereof through the aminoacetyl group is extremely stable, it is very much difficult to find an appropriate solvent to dissolve, disperse or swell the chitin favorably. Accordingly, the development pertaining to the utilization of chitin resources is far behind that of cellulose and other polysaccharides.

According to the recent research concerning the chitin or the chitin derivatives, films or fibers consisting of a regenerated chitin can be obtained by the acetylation of a chitosan by utilizing the properties of chitosan dissolved in an aqueous dilute acid solution. For instance, Japanese Patent Publication No. 19213/73 discloses a method for obtaining the film of the regenerated chitin by making a film of chitosan followed by acetylating the thus formed film in the solid phase. The method comprises a series of the following steps: at first, the chitosan is dissolved into an aqueous dilute acid solution and a film of a chitosan-salt obtained by drying the solution is immersed into an aqueous dilute alkali solution or a water-containing solvent of organic base to prepare the film of chitosan. After swelling the thus obtained film of chitosan in water, the swollen film of chitosan is soaked into a solvent such as ethanol, acetone, pyridine, etc. and is N-acetylated with an acetic acid in the presence of a dehydrating condensation agent of dicyclohexylcarbodiimide to obtain the film of the regenerated chitin. However, according to this method, it takes an extremely long period of time to complete the acetylation. Moreover, the published reference has an object of obtaining film-shaped articles consisting of the regenerated chitin and only suggests its application to an acoustic vibrator plate. Accordingly, it is still unsatisfactory from the view point of utilization of chitin resources.

The present inventor, during a series of his research into the chitin and the chitin derivatives, has found that a novel spherically shaped material at least the surface layer of which is insolubilized in water, acids, alkaline solutions and organic solvents can be produced from a de-N-acetylated chitin and that the spherically shaped material thus obtained can be employed as a separating material, a base material on which enzymes are immobilized, a material for dialysis and a material for adsorbent, etc. The spherically shaped material, especially the insolubilized surface thereof comprises an acylated product of the de-N-acetylated chitin.

Accordingly, an object of the invention is to spread out the effective utilization of the chitin resources. Another object of the invention is to provide a spherically shaped material comprising the acylated product of de-N-acetylated chitin, especially the spherical material at least the surface of which comprises the above-mentioned acylated product. Other objects of the invention will be apparent from the following descriptions.

Accordingly, the present invention provides a spherically shaped material at least the surface layer of which comprises an acylated product of de-N-acetylated chitin represented by the following general formula (I):

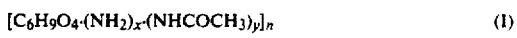

$$[C_6H_9O_4 \cdot (NH_2)_x \cdot (NHCOCH_3)_y]_n \quad (I)$$

wherein x is a number of 0.5 to 1.0 and $y = 1.0 - x$, or a salt thereof.

The above-mentioned "a spherically shaped material at least the surface layer of which comprises the acylated product" means a spherically shaped material of which the surface layer comprises the acylated product insoluble in water, acids, alkaline solutions and organic solvents and of which the interior comprises the abovementioned de-N-acetylated chitin or the salt thereof, or a spherically shaped material wholly or substantially wholly comprising the acylated product.

The spherical material of the present invention is chemically and physiologically stable and safe, and is excellent in permeability, adsorbability and bio-compatibility, and accordingly it is possibly applied to broad fields, for instance, as a material for capsules, a separating material such as fillers for chromatography, an adsorbing material, a material for catching heavy metals, a material for slow-releasing medicines, a base material for immobilizing enzymes, antibodies, antigens, etc., a material for ultrafiltration, a material for ionexchanger and the like.

The followings are the detailed explanation of the present invention.

The de-N-acetylated chitin represented by the formula (I) may be obtained by de-N-acetylating the chitin.

Chitin is a naturally produced mucopolysaccharide with the following formula (II):

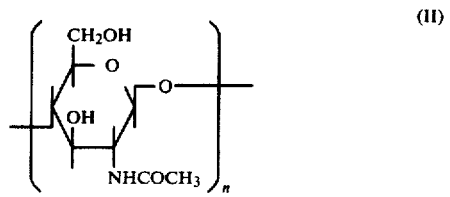

(II)

wherein n denotes the degree of polymerization.

Although n in the formula (II) can not be determined accurately because of the non-existence of a good solvent for suitably dissolving or dispersing chitin at present, n is believed to be commonly in the range of 50 to 10,000.

The de-N-acetylation of the chitin is achieved by heating the chitin in an aqueous concentrated solution of alkali such as sodium hydroxide, potassium hydroxide, etc. The de-N-acetylated chitin of the present invention has a degree of de-N-acetylation, on the average, of 0.5 to 1.0 per one pyranose ring, preferably 0.5 to 0.9.

The de-N-acetylated chitin thus obtained is soluble in an aqueous dilute acid solution. The aqueous dilute acid solution herein mentioned means an aqueous solution of an organic acid such as acetic acid, oxalic acid, etc. or of an inorganic acid such as hydrochloric acid, which has a concentration to dissolve the de-N-acetylated chitin of the invention.

In addition, it is noted that the de-N-acetylated chitin is also soluble in water in the form of a salt thereof. The salt of the de-N-acetylated chitin according to the invention includes an acetate and a hydrochloride, etc.

The spherically shaped material of the present invention is produced by adding an aqueous solution of the de-N-acetylated chitin into a solution of an anhydride of organic acid, as an acylating agent, containing a suspending agent and, if necessary, the organic acid followed by dispersing the aqueous solution of the de-N-acetylated chitin within the solution of the anhydride of organic acid.

The concentration of the de-N-acetylated material in the aqueous solution thereof affects the strength and the density of the spherically shaped material to be produced, and when it is higher, the spherically shaped material of larger strength and denser in structure is obtained, and such a spherically shaped material acts as a molecular sieve over a broad range of molecular diameter. Usually the concentration of the de-N-acetylated chitin in the aqueous solution may be 0.1 to 10% by weight, however, the concentration should be adequately adjusted according to the use and the property of the spherically shaped material of the present invention, and it is not necessarily restricted in the above-mentioned range.

When the viscosity of the aqueous solution of the de-N-acetylated chitin is high, sometimes it is difficult to obtain a spherically shaped material with a small diameter. In such a case, a viscosity-reducing agent such as ethylene glycol, glycerol, alcohol, etc. may be added in the above-mentioned aqueous solution.

In the process for producing the spherically shaped material according to the invention, the anhydride of organic acid and the organic acid are exemplified by aliphatic or aromatic organic acids with one to twenty carbon atoms and the anhydrides thereof, for example, acetic acid, propionic acid, butylic acid, valeric acid, benzoic acid and their anhydrides. The anhydride of organic acid in acylating the de-N-acetylated chitin may be one of the above-mentioned anhydrides or a mixture of more than one thereof. Although the amount of the acylating agent in the process of the present invention is not particularly restricted, it is usually 1 to 100 times by equivalent, preferably 5 to 20 times by equivalents per one equivalent of amino group of the de-N-acetylated chitin.

The above-mentioned anhydride of organic acid may be used as it is without any dilution, or may be diluted with the organic acid or with an organic solvent which does not react with the anhydride of organic acid, for instance, benzene, toluene, xylene, decalin, etc. for the purpose of controlling the reaction velocity or of facilitating the treatment of reaction product. In addition, in order to facilitate the control of the state of dispersed particles of the de-N-acetylated chitin in the above-mentioned solution of the anhydride of organic acid, the above-mentioned organic solvent is favorably added to the reaction system in an amount of 10 to 1,000 times by weight, preferably 10 to 500 times by weight of the above-mentioned solution of the de-N-acetylated substance.

The suspending agent used in the above-mentioned process is preferably selected from those of non-ionic type, for instance, polyoxyethylene sorbitan monoester, sorbitan monoester, i.e., polyoxyethylene sorbitan monooleate, polyoxyethylene sorbitan monostearate, polyoxyethylene sorbitan monopalmitate, polyoxyethylene sorbitan monolaurate, sorbitan monooleate, sorbitan monostearate, sorbitan monopalmitate and sorbitan monolaurate. The amount of the suspending agent may be usually selected optionally in the range of 0.001 to 10% by weight of the amount of the aqueous solution of the de-N-acetylated chitin. The suspending agent may be incorporated in the aqueous solution of the de-N-acetylated chitin as well as the solution of the anhydride.

The temperature of the acylation is 5° to 80° C., preferably 5° to 60° C.

Although the mechanism of the acylation of the present invention has not been elucidated, the reaction under the above-mentioned condition takes place at once when the aqueous solution of the de-N-acetylated chitin is brought into contact with the anhydride of organic acid. The reaction proceeds from the surface of the aqueous de-N-acetylated chitin solution to be formed into the spherically shaped material and forms an insoluble membrane consisting of the acylated product on the surface of the aqueous de-N-acetylated chitin solution. The interior of the thus formed membrane is still maintained at a state of the aqueous de-N-acetylated chitin solution. As the reaction still proceeds, the anhydride of organic acid diffuses into the interior via the above-mentioned membrane to bring out the acylating reaction therein gradually, and thereby the insolubilization of the interior is accompanied.

Accordingly, the present invention possibly can provide a spherically shaped material having its surface layer comprising the insoluble acylated product and its interior comprising the unreacted de-N-acetylated chitin or the salt thereof, depending on the degree of proceeding of the acylation.

The acylation predominantly takes place on N-position which is bonded to the carbon atom on 2-position of the pyranose ring of the de-N-acetylated chitin, as shown, for example, by the following formula (III) to (V). Another acylation may be also occur on O-position which is bonded to the carbon atom of 3 and/or 5 position of pyranose ring as in the following formulas (IV) and (V):

$$C_6H_8O_3\text{-(OH)-NHCOR'} \tag{III}$$

$$C_6H_8O_3\text{-(OCOR')-NHCOR'} \tag{IV}$$

$$C_6H_7O_2\text{-(OCOR')}_2\text{-NHCOR'} \tag{V}$$

wherein R' is an alkyl group or an aryl group.

The manner of carrying out the acylation reaction is to pour, preferably dropwise, the aqueous solution of de-N-acetylated chitin into the solution of the anhydride, or vice versa and then vigorously and homogeneously disperse the aqueous solution within the acylating solution by using a stirrer of blade type, static mixer, homogenizer, etc. In this manner, the reaction takes place at once from the surface of the drop of the aqueous solution of the de-N-acetylated chitin to form the insolubilized membrane of the acylated product. In addition, by spraying the aqueous solution of the de-N-acetylated chitin into a mist of the acid anhydride, the ultramicrospherically shaped material of the present invention may be also obtained, the surface layer of the ultramicrospherical droplets being infusibilized instantly by acylation. By the way, according to the present invention, a shaped material of hollow fiber type comprising the acylated product may be obtained by spinning the aqueous solution of the de-N-acetylated chitin through nozzles into a liquid containing the anhydride of organic acid to obtain a fiber of which surface layer is insolubilized, and then removing the soluble de-N-acetylated chitin occupying the interior of the fiber from the insolubilized product.

The size of the spherical product of the invention can be adjusted within a broad range of its diameter of about 0.1 to 5,000 μm, and the product is shperical such that the maximum diameter of the spherical product is about 1.0 to 1.3 times of the minimum diameter thereof in the wet state. The thickness and compactness of the insolubilized surface layer are variable by controlling the concentration of the aqueous solution of the de-N-acetylated chitin, the time period and the temperature of the reaction, within a range of the thickness of 0.1 to 1,000 μm and compactness range with a permeable threshold of from 500 to 100,000 in molecular weight.

The spherically shaped material of the present invention thus obtained may be subjected to the cross-linking treatment, if necessary. One of the cross-linking treatments is as follows.

In the cross-linking treatment, at first, the moisture content of the spherical material is made to be 2 to 3 times by weight of the material at a dried state. Then the material is soaked in an aqueous sodium hydroxide solution of a concentration more than 40% by weight and of an amount of more than 2 times, preferably 4 to 30 times by weight of the dried material at a temperature of lower than 15° C. for one to 5 hours. After that, an excess sodium hydroxide solution is removed and the material is left to stand at a soaked state in the aqueous sodium hydroxide solution of an amount of 3 to 6 times by weight of the dried material at a temperature of 0° to 10° C. for one to 24 hours to obtain a pre-treated material by alkali. After optionally freeze-drying the pre-treated material at a temperature of 0° to −30° C. for one to 24 hours, the pre-treated material is then dispersed in an aqueous solution or an organic solvent containing a cross-linking agent in an amount of 0.1 to 3 times by mole, preferably 0.5 to 2 times by mole per one pyranose ring and is made to react at a temperature of lower than 15° C. for 5 to 48 hours. After the reaction is over, the reaction product is washed and neutralized to obtain a cross-linked material. As the cross-linking agent, epoxy-type agents such as epichlorohydrin, epibromohydrin, 2,3-dibromopropanol and 2,3-dichloropropanol are suitable. The degree of cross-linking may be sufficient at up to 0.3 per one unit of pyranose ring.

In addition, when the interior of the spherically shaped material is not acylated or insolubilized, the cross-linking agent may be selected from aldehydes such as formaldehyde, glyoxal and glutaraldehyde which form a Schiff base with the de-N-acetylated chitin in the interior of the spherical material.

The spherically shaped material of the invention is composed of the chemically and biologically stable and safe acylated product and has a substance-permeable property, it is applicable to a broad range of uses. Examples of the uses are, for instance, the separation and purification of polysaccharides, proteins, and the mixture thereof, etc. by immersing the material into an aqueous solution of polysaccharides, proteins or the mixture thereof of various molecular weight and dispersing only the substances of molecular weight less than a predetermined value into the material. Moreover, when the material has amino groups in its structure, it is also utilizable as an ion-exchange body. Because of the stability and the safety of the material to living bodies, the use of the material in the fields of concerns of living bodies, for instance, for blood perfusion, for pad to surgical injuries, for an adsorbent of gastrointestinal toxins after internally administered or for the coating agent of the adsorbent, is possible.

In addition, in the case where the material is used for the contact with blood, it is more preferable to adjust the acylation to leave some amino groups standing in free state and then to make a polyion with an anti-thromobolytic agent such as heparin, chitosan sulfate, chitin sulfate, etc.

Also, it is possible to confine several useful functional substances within the spherically shaped material of the present invention. For instance, by confining several ion-exchange resins within the shaped material, a novel ion-exchange body coated by a chitinic membrane having a limited ion-exchanging activity only to substance with molecular weight less than a predetermined value is obtained, and by coating an adsorbent such as activated carbon with the material of the present invention, an adsorbent having a novel functional ability never known before is obtained.

As has been explained, the present invention is really epoch-making by which chitin becomes utilizable in infinitely developing fields of application.

The present invention will be explained in more detail referring to the following non-limiting Examples.

EXAMPLE 1

A solution of 5 g of de-N-acetylated chitin with a degree of de-N-acetylation of 0.8 dissolved in 200 ml of an aqueous 2% acetic acid solution was equally divided into two portions. Into one of the portions, 1% by weight of sorbitan monooleate and 20% by weight of ethanol were added, and into the other portion, 20% by weight of ethanol was solely added, the former portion being called as A liquid and the latter being called as B liquid. Separately, two sets of dispersing media were prepared by dissolving each 5 g of polyoxyethylene sorbitan monooleate and 10 g of acetic anhydride as an acylating agent into 2 liters of toluene in a dispersion vessel provided with a bow-type stirrer. Then, the above-mentioned A liquid and B liquid were respectively added to the respective dispersing media while stirring at 1,000 r.p.m. at room temperature for one hour to acylate the A and B liquids. On adding one liter of ethanol to the respective reaction mixture while agitating, clear spherical materials were formed and sedimented. After collecting the materials by filtration and washing the collected materials with ethanol, the thus obtained sedimented materials were dispersed into one liter of distilled water and the pH of the medium of the dispersion was adjusted to 8.0. After collecting the thus treated materials by filtration and washing off sodium acetate and sodium hydroxide which adhered to the materials with distilled water, gel-like spherical materials of the present invention were obtained having a diameter of 50 to 150 microns.

The gel-like materials prepared from both liquids of A and B were insoluble in an aqueous 5% by weight solution of acetic acid, and elastic in property containing water therein. After drying, both the materials prepared from liquid A and liquid B did not show an infrared absorption band of 1,500 to 1,530 cm$^{-1}$ due to amino group, which showed the materials were completely acylated. Their elementary analyses gave the following values:

| Product | C | H | O | N (%) |
|---|---|---|---|---|
| from A | 46.5 | 6.4 | 40.4 | 6.8 |
| from B | 46.3 | 6.5 | 40.3 | 6.7 |

These values show fairly good coincidence with those of chitin.

EXAMPLE 2

The two kinds of gel-like shaped materials A and B, A being prepared from liquid A of EXAMPLE 1 containing a surfactant and B being prepared from liquid B of EXAMPLE 1 not containing a surfactant were separately filled up in two columns of 2 cm in inner diameter at a height corresponding to the volume of 150 ml in the column. The columns were subjected to a test of separating ability of the materials A and B by the following procedures:

Each 20 mg of blue-dextran of molecular weight of 2,000,000, of dextran (i) of molecular weight of 100,000, of dextran (ii) of molecular weight of 10,000 and of glucose were dissolved into 2 ml of distilled water as solutes, and the solution was developed on the above-mentioned column. Distilled water was poured onto the column at a rate of 1 ml/min and the effluent was collected every 5 ml in portions to analyze the solutes therein. The results of analyses are shown in Table 1.

As is seen in Table 1, the shaped materials according to the present invention exhibited their separating ability to the mixture of blue dextran, two dextrans (i) and (ii) and glucose in water, thus showing the effectiveness as a column-filling material for chromatography. Especially, the shaped material A is noticeable in having a separating ability to dextran of molecular weight of 100,000.

TABLE 1

Results of Chromatographic Separation

| | Position of the solute in the effluent shown by the volume of the effluent (ml) | |
|---|---|---|
| Solute | Shaped material A | Shaped material B |
| Blue-dextran | 55 to 65 | 55 to 65 |
| Dextran (i) | 80 to 90 | 55 to 65 |
| Dextran (ii) | 90 to 100 | 90 to 100 |
| Glucose | 150 to 160 | 155 to 165 |

EXAMPLE 3

The gel-like spherical products of the invention were prepared by acylating the A liquid of EXAMPLE 1 with propionic anhydride as in the manner of EXAMPLE 1. The reaction time was prolonged to three hours.

The gel-like products thus obtained were similarly acylated in the surface and interior thereof completely, and did not dissolve into an aqueous 5% by weight of acetic acid solution but maintained their spherical shape.

The size of the product was in the range of 50 to 150 μm, and the ratio of the maximum diameter to the minimum diameter in each product was in the range of about 1.0 to 1.1.

EXAMPLE 4

One gram of de-N-acetylated chitin with a degree of de-N-acetylation of 0.9 was dissolved into 100 ml of an aqueous 2% by weight of acetic acid solution. Methanol of 100 ml was further added into the solution to obtain a homogeneous solution. Separately, 20 g of polyoxyethylene sorbitan monooleate and 5 g of acetic anhydride were dissolved into 3 liters of toluene in a dispersing vessel provided with a bow-type stirrer.

The above solution of de-N-acetylated chitin of 100 ml was added and acylated in the dispersing vessel while stirring at 10,000 r.p.m. at room temperature for two hours. Then adding 2 liters of ethanol, a clear solution and a precipitate were separated. After filtering the precipitate by a centrifuge followed by washing with ethanol three times, the obtained precipitate was dispersed into 1 liter of distilled water. After the centrifugal filtration and several washings, the fine spherical materials of 1-10 μm in size were obtained, of which surface and interior were completely acylated.

From the electromicroscopic observation, the ratio of the maximum diameter to the minimum diameter of the material was found in the range of 1.0 to 1.1. The material did not dissolve into an aqueous 5% by weight of acetic acid solution.

EXAMPLE 5

Three kinds of de-N-acetylated chitin, each having a degree of de-N-acetylation of 0.5, 0.7 and 0.9, respectively, were treated as in EXAMPLE 1, however, changing the time period of acylation. Each kind of obtained spherical materials had the rate of the maximum diameter to the minimum diameter of 1.1 to 1.3, 1.0 to 1.1 and 1.0 to 1.1, respectively. By changing the reaction time for acylation, a spherically shaped material of which surface layer comprises the insoluble acylated product and of which interior comprises the soluble de-N-acetylated chitin was obtained. This is shown in FIGURE of an attached drawing, which represents the relation of an ion-exchange capacity of the obtained shaped material to the reaction time of acylation. The ion-exchange capacity was determined by a batch method.

From the FIGURE, it is understood that the ion-exchange capacity is decreased with the lapse of reaction time. As the ion-exchange capacity depends on the amount of the free amino group contained in the shaped material, the gradual decrease of the ion-exchange capacity corresponds to the gradual increase of the acylation of the amino group, that is, the acylation and insolubilization of the shaped material proceed from the surface thereof while leaving the amino group-containing de-N-acetylated chitin in the interior thereof. In this manner, the present invention can provide the spherically shaped material at least the surface layer of which is acylated and insolubilized and the shaped material which has an optional ion-exchange capacity by changing the reaction time for acylation.

Further, it is proved from the following experiments that the present invention can provide the spherically shaped material of which surface comprises the insoluble product and of which interior comprises the soluble chitin derivative.

The spherical material obtained by acylating the above-mentioned de-N-acetylated chitin with the degree of de-N-acetylation of 0.9 for 15 minutes was immersed into an aqueous 5% by weight of acetic acid solution. The material maintained its spherical shape in the acetic acid solution. After the filtration, the filtrate was neutralized with 1 N-sodium hydroxide solution not to find any precipitate but a clear solution. This shows that the material was insoluble in the dilute acidic solution and the soluble de-N-acetylated chitin contained in the inside of the material was not dissolved into the acidic solution through the acylated and insolubilized surface membrane of the material.

The insoluble surface membrane was crushed in another aqueous 5% by weight of acetic acid solution. By the centrifugal filtration, the insoluble pieces of the membrane and the filtrate were separated. The insoluble pieces were found not to have 1500 to 1530 cm$^{-1}$ of absorption band of amino group from the infrared inspection, which shows that the insoluble membrane was completely acylated and any amino group was not present in the surface of the obtained shaped material. The separated filtrate was neutralized with 1 N-sodium hydroxide solution to find an unclear solution. Then, centrifugally filtering the unclear solution followed by washing, the obtained precipitate was freeze-dried. The freeze-dried product was observed by the infrared inspection to have the absorption band of amino group of 1,500 to 1,530 cm$^{-1}$, which shows that the precipitate is the de-N-acetylated chitin originally present in the interior of the obtained shaped material.

EXAMPLE 6

The spherical gel-like shaped material obtained in Example 1 was dehydrated by centrifugation until the water content of the material became 2 g per 1 g of dried weight of the material. The semi-dried material was put into 20,000 times by weight of an aqueous 45% sodium hydroxide solution at a temperature of 10° C. and the mixture was mixed for 3 hours. The thus treated material was further treated to be deprived of excessive alkali until the alkali content of the material became three times by weight of the dry weight of the material. After keeping the thus obtained material at a temperature of 0° for 2 hours, it was frozen at −25° C. for one hour to obtain the material pre-treated by alkali.

An amount of epibromohydrin corresponding to 2 times by mol of the dried material pre-treated by alkali was dissolved in an amount of isopropyl alcohol of 50 times by weight of the dried material pre-treated by alkali, and into the thus resulted solution kept at a temperature of 0° to 5° C. the above-mentioned frozen material pre-treated by alkali was added to carry out a cross-linking reaction for 5 hours under agitation and the reaction was further carried out at 20° C. for 5 hours. Then, the reaction mixture was filtered and after washing the precipitate with ethanol, the precipitate was dispersed in a distilled water. The dispersion was then neutralized with a 1 N-hydrochloric acid solution while cooling.

The neutralizate was filtered and the residue was washed with distilled water. It was found that the cross-linked product maintained its original spherical shape and that the product had not been de-N-acetylated from the infrared absorption spectroscopy. The degree of cross-linkage of the product was found to be 0.15 per one pyranose ring from its elementary analytical data.

What is claimed is:

1. A spherically shaped material at least the surface layer of which comprising an acylated product of de-N-acetylated chitin or a salt thereof.

2. The material according to claim 1, of which interior comprises the de-N-acetylated chitin or the salt thereof.

3. The material according to claim 1, which wholly or substantially wholly comprises the acylated product.

4. The material according to claim 1 or 2, wherein the degree of de-N-acetylation of the de-N-acetylation chitin is 0.5 to 1.0, preferably 0.5 to 0.9.

5. The material according to claim 1, which has a diameter of 0.1 to 5,000 μm and a ratio of the maximum diameter to the minimum diameter of 1.0 to 1.3.

6. The material according to claim 1, wherein the acylated product and/or the de-N-acetylated chitin within the material is further crosslinked and the degree of the crosslinking is up to 0.3 per pyranose ring.

7. The material according to claim 1 or 2, wherein the salt is an acetate or a hydrochloride of the de-N-acetylated chitin.

8. A process for producing a spherically shaped material of an acylated product of de-N-acetylated chitin, comprising dispersing an aqueous solution of a de-N-acetylated chitin or a salt thereof dropwise as minute droplets into an anhydride of an organic acid having the same acyl group as in said acylated product and containing a suspending agent, thereby acylating said minute droplets of said aqueous solution of the de-N-acetylated chitin to obtain a spherically shaped material.

9. The process according to claim 8, wherein the aqueous solution is an aqueous diluted acid solution.

10. The process according to claim 8 or 9, wherein the concentration of the de-N-acetylated chitin in the aqueous solution is 0.1 to 10% by weight.

11. The process according to claim 8, wherein the aqueous solution of the de-N-acetylated chitin further contains a suspending agent.

12. The process according to claim 8, wherein said anhydride of an organic acid is an anhydride of an organic acid having one to twenty carbon atoms or a mixture of said anhydrides.

13. The process according to claim 8, wherein the amount of said anhydride of said organic acid is 1 to 100 equivalents per equivalent of amino group of said de-N-acetylated chitin.

14. The process according to claim 8, wherein the suspending agent is selected from the group consisting of polyoxyethylene sorbitan monoesters and sorbitan monoesters.

15. The process according to claim 8, wherein the amount of said suspending agent is 0.001 to 10% by weight of the aqueous solution of the de-N-acetylated chitin.

16. The process according to claim 8, wherein the solution of the anhydride of said organic acid further contains an organic acid.

17. The process according to claim 8, wherein said anhydride of said organic acid further contains an organic solvent inert to the reactants in the system and the amount of said organic solvent is 10 to 1,000 times by weight, preferably 10 to 500 times by weight of the amount of said aqueous solution of said de-N-acetylated chitin.

18. The process according to claim 8, wherein after said acylating, the thus obtained acylated product is further subjected to a cross-linking treatment.

19. The process according to claim 8, wherein the aqueous solution of the de-N-acetylated chitin contains a viscosity-reducing agent.

* * * * *